United States Patent
Gerster et al.

(10) Patent No.: US 7,560,502 B2
(45) Date of Patent: Jul. 14, 2009

(54) FUNCTIONALIZED ESTERS, AMIDES OR URETHANES OF PERFLUORINATED ALCOHOLS OR AMINES AS SURFACE MODIFIERS

(75) Inventors: Michèle Gerster, Binningen (CH); Manuel Mihalic, Grenzach-Wyhlen (DE); Armin Schneider, Freiburg (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 24 days.

(21) Appl. No.: 11/883,009

(22) PCT Filed: Jan. 30, 2006

(86) PCT No.: PCT/EP2006/050508

§ 371 (c)(1),
(2), (4) Date: Jul. 25, 2007

(87) PCT Pub. No.: WO2006/082166

PCT Pub. Date: Aug. 10, 2006

(65) Prior Publication Data

US 2008/0146742 A1 Jun. 19, 2008

(30) Foreign Application Priority Data

Feb. 7, 2005 (EP) .................... 05100836

(51) Int. Cl.
*C08K 5/43* (2006.01)
*D06M 15/00* (2006.01)
*B01J 8/36* (2006.01)

(52) U.S. Cl. ............. 524/169; 560/111; 524/199; 524/208; 524/260; 524/462

(58) Field of Classification Search ........... 524/208, 524/260; 560/111
See application file for complete search history.

(56) References Cited

U.S. PATENT DOCUMENTS 3,478,087 A 11/1969 McGrath et al. ............ 260/475
5,520,845 A * 5/1996 Auman et al. ............ 252/299.4
6,127,485 A 10/2000 Klun et al. ................. 525/199
2004/0176526 A1* 9/2004 Shimo-Ohsako et al. .... 524/514

FOREIGN PATENT DOCUMENTS

| EP | 0088389 | | 9/1983 |
| JP | 02-225522 A | * | 9/1990 |
| JP | 04-360852 | | 12/1992 |
| JP | 07-224007 | | 8/1995 |
| JP | 08-208836 | * | 8/1996 |

OTHER PUBLICATIONS

Machine translation of JP 08-208836.*
New copolyimide membranes for the pervaporation of trichloroethylene from water.*
Patent Abstracts of Japan Publication No. 04360852, (Dec. 1992).
Derwent Abstract 1995-325509 [42] for JP 07224007, (Aug. 1995).

* cited by examiner

*Primary Examiner*—Marc S. Zimmer
*Assistant Examiner*—John Uselding
(74) *Attorney, Agent, or Firm*—Tyler A. Stevenson

(57) ABSTRACT

The invention describes a composition comprising a) an organic material which is susceptible to oxidative, thermal or light-induced degradation, and b) at least one melt additive of a compound of the formula I R1(I)R3XR2 wherein the general symbols are as defined in claim 1. The compounds of the formula I are useful as reducers of surface energy for organic materials, for example, for increasing the oil and water repellency of organic materials.

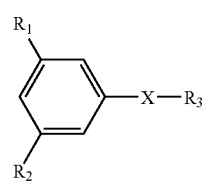

(I)

16 Claims, No Drawings

FUNCTIONALIZED ESTERS, AMIDES OR URETHANES OF PERFLUORINATED ALCOHOLS OR AMINES AS SURFACE MODIFIERS

The present invention relates to compositions comprising an organic material, preferably a synthetic polymer, susceptible to oxidative, thermal or light-induced degradation and to esters, amides or urethanes of perfluorinated alcohols as reducer of surface energy of these materials, for example as oil and water repellency agents for organic materials.

The use of various fluorochemical compositions on fibers and fibrous substrates, such as for example textiles, carpets, paper, leather and non-woven webs to impart oil and water repellency is known for example in U.S. Pat. No. 6,127,485. This reference discloses hydrophobic and oleophobic fibers, films and molded articles comprising synthetic organic polymer wherein dispersed within the fiber, fabric or molded article and present at the surface of the fiber, fabric or molded article are fluorochemical compounds.

The known fluorochemicals do not satisfy in every respect the high requirements which a melt additive is required to meet as reducers of surface energy for organic materials, for example, for increasing the oil and water repellency of organic materials.

It has now been found that esters, amides or urethanes of perfluorinated alcohols are useful for various technical applications such as for example for increasing the oil and water repellency of organic materials like for example synthetic polymers.

The present invention therefore provides a composition comprising
a) an organic material which is susceptible to oxidative, thermal or light-induced degradation, and
b) at least a compound of the formula I

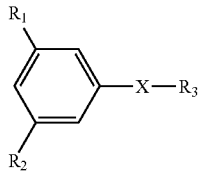

(I)

wherein
$R_1$ is —$NO_2$, —N=CH—$R_4$ or

$R_2$ is —$NO_2$, —N=CH—$R_4$,

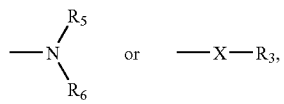

$R_3$ is a fluorine containing group,
$R_4$ is $C_1$-$C_{25}$alkyl, $C_3$-$C_{25}$alkenyl, unsubstituted or $C_1$-$C_4$alkyl substituted phenyl;
$R_5$ is hydrogen, —Y—$R_7$,

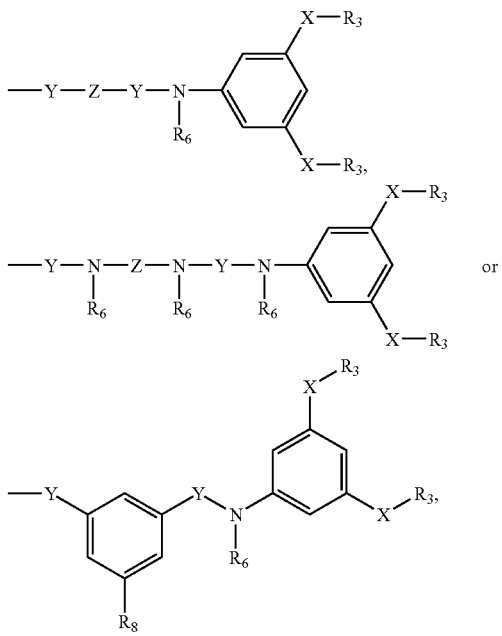

or $R_6$ is hydrogen, $C_1$-$C_8$alkyl or benzyl,
$R_7$ is $C_1$-$C_{25}$alkyl, $C_2$-$C_{25}$alkenyl, unsubstituted or with $C_1$-$C_4$alkyl or $C_1$-$C_4$alkanoylamino substituted phenyl; unsubstituted or $C_1$-$C_4$alkyl substituted phenylamino;
$R_8$ is —$NO_2$, —N=CH—$R_4$ or

$R_9$ is hydrogen or —Y—$R_7$,

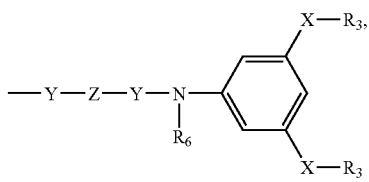

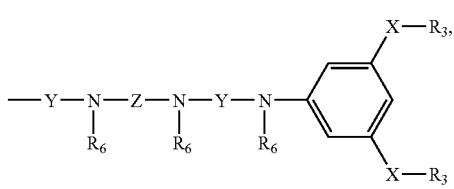

-continued

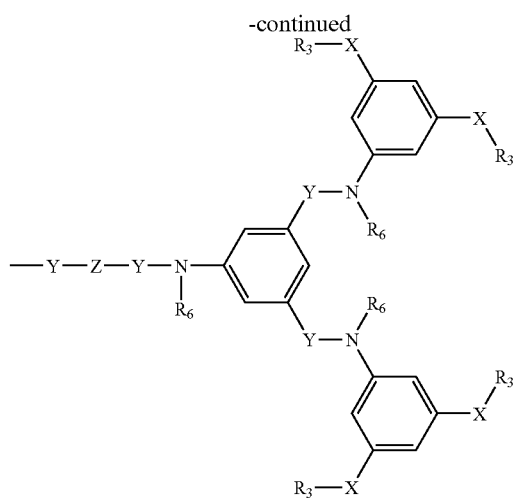

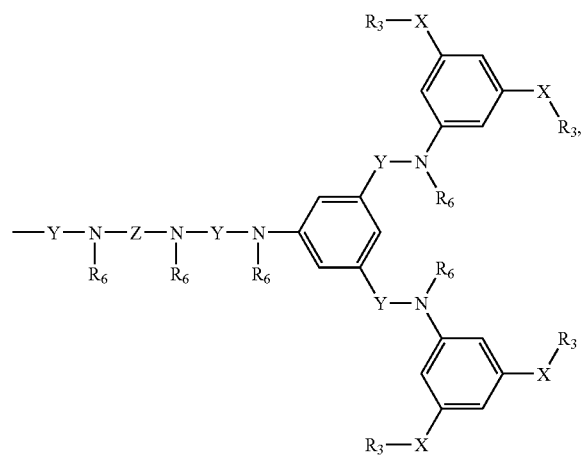

$R_{10}$ is hydrogen, $C_1$-$C_8$alkyl or benzyl,
X is

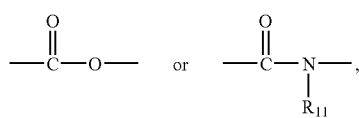

$R_{11}$ is hydrogen, $C_1$-$C_8$alkyl or benzyl,
Y is

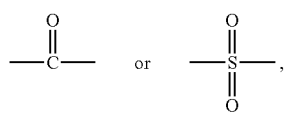

Z is $C_1$-$C_{25}$alkylene, 1,2-phenylene, 1,3-phenylene, 1,4-phenylene or

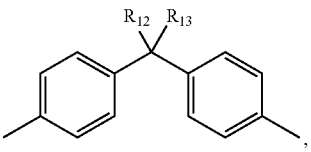

or and $R_{12}$ and $R_{13}$ are each independently of one another hydrogen, $C_1$-$C_{12}$alkyl or phenyl, or $R_{11}$ and $R_{12}$ together with the linking carbon atom, form a $C_5$-$C_8$cycloalkylidene ring which is unsubstituted or substituted by 1 to 3 $C_1$-$C_4$alkyl groups.

A fluorine containing group is a branched or unbranched radical, which contains at least one fluoro atom, for example $C_1$-$C_{25}$fluoroalkyl, $C_1$-$C_{25}$fluoroalkyl is for example fluoromethyl, 2-fluoroethyl, 3-fluoropropyl, 4-fluorobutyl, 5-fluoropentyl, 6-fluorohexyl, 7-fluoroheptyl, difluoromethyl, trifluoromethyl, pentafluoroethyl, pentafluorobutyl or perfluoroalkyl such as for example —$CH_2CH_2(CF_2)_7CF_3$ or —$CH_2CH_2(CF_2)_3CF_3$.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

Alkenyl having 3 to 25 carbon atoms is a branched or unbranched radical such as, for example, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. Preference is given to alkenyl having 3 to 18, especially 3 to 12, for example 3 to 6, especially 3 to 4 carbon atoms.

$C_1$-$C_4$Alkyl-substituted or $C_1$-$C_4$alkanoylamino substituted phenyl, which contains preferably from 1 to 3, especially 1 or 2, alkyl or alkanoylamino groups, is, for example, o-, m- or p-methyl phenyl, 2,3-dimethylphenyl, 2,4-dimethyl phenyl, 2,5-dimethyl phenyl, 2,6-dimethylphenyl, 3,4-dimethylphenyl, 3,5-dimethylphenyl, 2-methyl-6-ethylphenyl, 4-tert-butylphenyl, 4-tert-pivaloylaminophenyl, 2-ethylphenyl or 2,6-diethylphenyl.

$C_1$-$C_4$Alkyl-substituted phenylamino, which contains preferably from 1 to 3, especially 1 or 2, alkyl groups, is, for example, o-, m- or p-methylphenylamino, 2,3-dimethylphenylamino, 2,4-dimethylphenylamino, 2,5-dimethylphenylamino, 2,6-dimethylphenylamino, 3,4-dimethylphenylamino, 3,5-dimethylphenylamino, 2-methyl-6-ethylphenylamino, 4-tert-butylphenylamino, 2-ethylphenylamino or 2,6-diethylphenylamino.

Alkanoylamino having up to 4 carbon atoms is a branched or unbranched radical, for example formylamino, acetylamino, propionylamino, butanoylamino or pivaloylamino.

A $C_5$-$C_8$cycloalkylidene ring substituted by $C_1$-$C_4$alkyl, which contains preferably from 1 to 3, especially 1 or 2, branched or unbranched alkyl group radicals, is, for example, cyclopentylidene, methylcyclopentylidene, dimethylcyclopentylidene, cyclohexylidene, methylcyclohexylidene, dimethylcyclohexylidene, trimethylcyclohexylidene, tertbutylcyclohexylidene, cycloheptylidene or cyclooctylidene. Preference is given to cyclohexylidene and tert-butylcyclohexylidene.

Interesting compositions comprise as component (b) at least a compound of the formula I wherein $R_2$ is —X—$R_3$, $R_3$ is $C_1$-$C_{25}$fluoroalkyl, X is

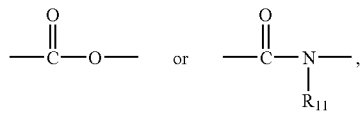

and

$R_{11}$ is hydrogen or $C_1$-$C_4$alkyl.

Preferred compositions comprise as component (b) at least a compound of the formula I wherein $R_3$ is $C_1$-$C_{25}$fluoroalkyl.

Preference is also given to compositions comprising as component (b) at least a compound of the formula I wherein $R_6$ and $R_{10}$ are hydrogen.

Particular preference is given to compositions comprising as component (b) at least a compound of the formula I wherein $R_7$ is $C_1$-$C_{18}$alkyl, $C_2$-$C_{18}$alkenyl, unsubstituted or with $C_1$-$C_4$alkyl or $C_1$-$C_4$alkanoylamino substituted phenyl; unsubstituted or $C_1$-$C_4$alkyl substituted phenylamino.

Of interest are compositions comprising as component (b) at least a compound of the formula I wherein $R_{12}$ and $R_{13}$ are each independently of one another hydrogen or $C_1$-$C_4$alkyl, or $R_{12}$ and $R_{13}$ together with the linking carbon atom, form a cyclohexylidene ring.

Also of interest are compositions comprising as component (b) at least one compound of the formula I, wherein $R_1$ is —$NO_2$, —N=CH—$R_4$ or

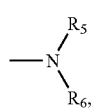

$R_2$ is —$NO_2$, —N=CH—$R_4$,

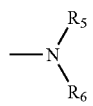

or —X—$R_3$, $R_3$ is —$CH_2CH_2(CF_2)_7CF_3$ or —$CH_2CH_2(CF_2)_3CF_3$, $R_4$ is $C_4$-$C_{12}$alkyl, $C_4$-$C_{12}$alkenyl, unsubstituted or $C_1$-$C_4$alkyl substituted phenyl;

$R_5$ is hydrogen, —Y—$R_7$,

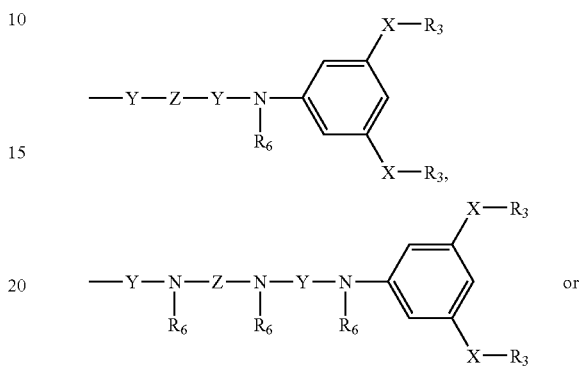

$R_6$ is hydrogen, $R_7$ is $C_1$-$C_8$alkyl, $C_2$-$C_8$alkenyl, phenyl or phenylamino, $R_8$ is —$NO_2$, —N=CH—$R_4$ or

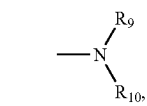

$R_9$ is hydrogen, —Y—$R_7$,

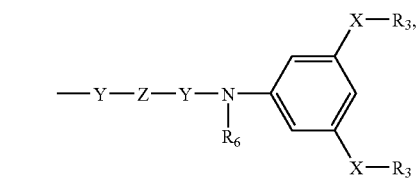

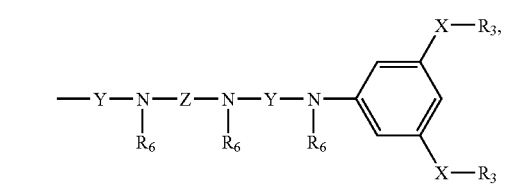

-continued

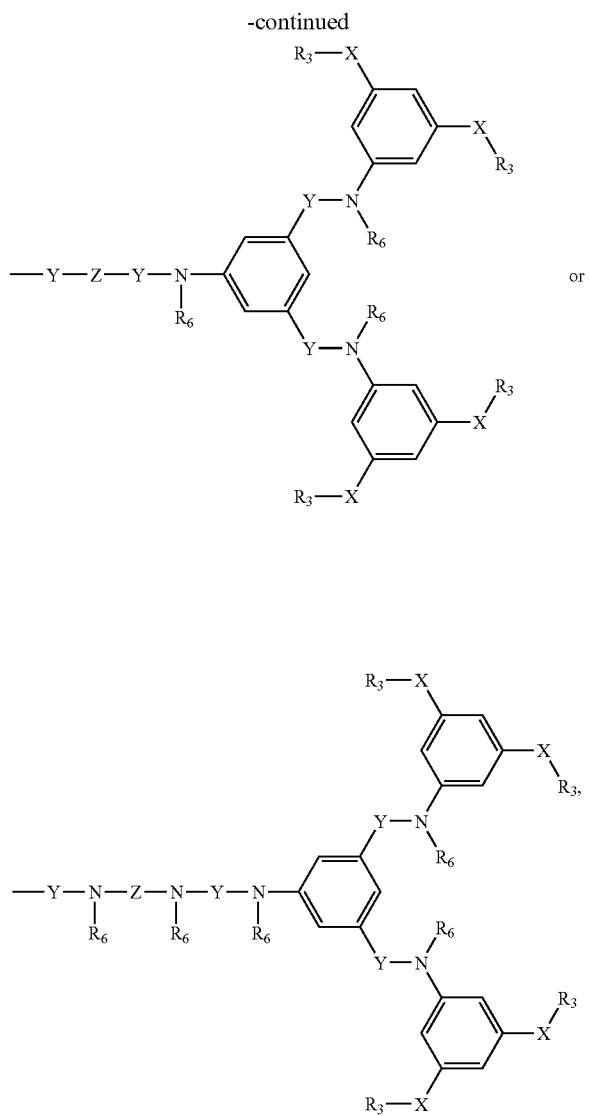

$R_{10}$ is hydrogen,

X is

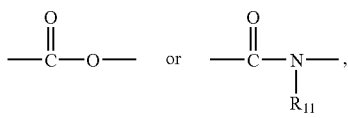

$R_{11}$ is hydrogen,

Y is

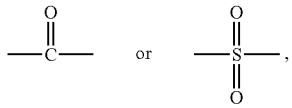

Z is $C_4$-$C_{12}$alkylene, 1,3-phenylene, 1,4-phenylene or

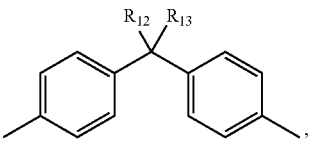

and $R_{12}$ and $R_{13}$ are hydrogen.

The compounds of the formula I can be prepared in per se known manner, for example by esterification or amidation of a carboxylic acid with an alcohol or amide. The urethanes are preferably prepared by the reaction of an isocyanate with an alcohol.

The compounds of the formula I are suitable as oil and water repellency agents for organic materials. Examples of organic materials which may be present in the compositions of the invention are following materials:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/ propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are natural, semi-synthetic or, preferably, synthetic polymers.

Particularly referred organic materials are synthetic polymers, most preferably thermoplastic polymers. Especially preferred organic materials are polyacetals, polyolefins such as polypropylene or polyethylene, polyether/polyurethanes, polyesters such as polybutylene terephthalate, polycarbonates or polyamides.

To be singled out for special mention is the efficacy of the compounds of the formula I [component (b)] as reducers of surface energy of the organic materials. Organic materials with low surface energy have intrinsically better properties like for example water and oil repellency, hydrophobicity, barrier properties, easy to clean, self cleaning, antigraffiti or solvent resistance.

The compounds of the formula I will preferably be added to the organic material in concentrations of 0.01 to 10%, preferably 0.01 to 2%, typically 0.1 to 2%, based on the weight of said material.

In addition to components (a) and (b), the compositions of the invention may comprise further additives, such as for example the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutyl phenol, 2,6-dicyclopentyl-4-methyl phenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethyl phenols, for example 2,4-dioctylthiomethyl-6-tert-butylphenol, 2,4-dioctylthiomethyl-6-methylphenol, 2,4-dioctylthiomethyl-6-ethyl phenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example $\alpha$-tocopherol, $\beta$-tocopherol, $\gamma$-tocopherol, $\delta$-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methyl phenol), 4,4'-thiobis(3,6-di-sec-amyl phenol), 4,4'-bis(2,6-dimethyl-4-hydroxyphenyl)-disulfide.

1.6. Alkylidenebisphenols, for example 2, 2'-methylenebis (6-tert-butyl-4-methylphenol), 2,2'-methylenebis(6-tert-butyl-4-ethylphenol), 2,2'-methylenebis[4-methyl-6-($\alpha$-methylcyclohexyl)-phenol], 2,2'-methylenebis(4-methyl-6-cyclohexylphenol), 2,2'-methylenebis(6-nonyl-4-methyl phenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-(α,α-dimethylbenzyl)-4-nonylphenol], 4,4'-methyllenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methyl phenol, 1,1,3-tris(5-tert-butyl-4-hydroxy-2-methyl phenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methyl phenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methyl phenyl)pentane.

1.7. O-, N- and S-benzyl compounds, for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecyl mercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethyl benzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenyl methane, 1,2-bis[(2-methyl phenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethyl hexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenyl benzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$—]$_2$, where R=3'-tert-butyl-4'-hydroxy-5'-2H-benzotriazol-2-yl phenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butyl phenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tertoctylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6- tetramethylpiperidine, 5-(2-ethyl hexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethyl piperazine-3-one-4-yl)amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethyl phenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydro-oxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)-pentaerythritol diphosphite, bis(2,4,6-tris(t-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzyl hydroxylamine, N,N-diethyl hydroxylamine, N,N-dioctylhydroxylamine, N,N-dilaurylhydroxylamine, N,N-ditetradecyl hydroxylamine, N,N-dihexadecylhydroxylamine, N,N-dioctadecyl hydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptyinitrone, N-lauryl-alpha-undecylnitrone, N-tetradecyl-alpha-tridecyl nnitrone, N-hexadecyl-alpha-pentadecyl nitrone, N-octadecyl-alpha-heptadecyl nitrone, N-hexadecyl-alpha-heptadecyl nitrone, N-ocatadecyl-alpha-pentadecyl nitrone, N-heptadecyl-alpha-hepta-decylnitrone, N-octadecyl-alpha-hexadecyl nitrone, nitrone derived from N N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecyl mercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244;

U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butyl benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one], 3-(4-acetoxy-3,5-dimethylphenyl)-5,7-di-tert-butylbenzofuran-2-one, 3-(3,5-dimethyl-4-pivaloyloxyphenyl)-5,7-di-tert-butyl benzofuran-2-one, 3-(3,4-dimethylphenyl)-5,7-di-tert-butyl benzofuran-2-one, 3-(2,3-dimethyl phenyl)-5,7-d i-tert-butyl benzofuran-2-one, 3-(2-acetyl-5-isooctyl phenyl)-5-isooctylbenzofuran-2-one.

The further additives are typically used in concentrations of 0.01 to 10%, based on the total weight of the material to be treated.

Preferred compositions of the invention comprise, as other additives phenolic antioxidants, light stabilizers and/or processing stabilizers.

Incorporation of component (b) and, if desired, further additives into the synthetic polymers is carried out by known methods, for example before or during moulding or else by applying the dissolved or dispersed compounds to the synthetic polymer, if appropriate with subsequent slow evaporation of the solvent.

The present invention also relates to a composition in the form of a masterbatch or concentrate comprising component (a) in an amount of from 5 to 90% and component (b) in an amount of from 5 to 80% by weight.

Component (b) and, if desired, further additives, can also be added before or during polymerisation or before crosslinking.

Component (b), with or without further additives, can be incorporated in pure form or encapsulated in waxes, oils or polymers into the synthetic polymer.

Component (b), with or without further additives, can also be sprayed onto the synthetic polymer. It is able to dilute other additives (for example the conventional additives indicated above) or their melts so that they too can be sprayed together with these additives onto the polymer. Addition by spraying on during the deactivation of the polymerization catalysts is particularly advantageous, it being possible to carry out spraying using, for example, the steam used for deactivation.

In the case of spherically polymerized polyolefins it may, for example, be advantageous to apply component (b), with or without other additives, by spraying.

The synthetic polymers prepared in this way can be employed in a wide variety of forms, for example as foams, films, fibres, tapes, moulding compositions, as profiles or as binders for coating materials, especially powder coatings, adhesives, putties or especially as thick-layer polyolefin mouldings which are in long-term contact with extractive media, such as, for example, pipes for liquids or gases, films, fibres, geomembranes, tapes, profiles or tanks.

The preferred thick-layer polyolefin mouldings have a layer thickness of from 1 to 50 mm, in particular from 1 to 30 mm, for example from 2 to 10 mm.

The compositions according to the invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Of special interest are compositions comprising as component (a) fibers and nonwovens.

Thus, a further embodiment of the present invention relates to a shaped article, in particular a film, pipe, profile, bottle, tank or container, fiber containing a composition as described above.

A further embodiment of the present invention relates to a molded article containing a composition as described above. The molding is in particular effected by injection, blow, compression, roto-molding or slush-molding or extrusion.

The present invention also relates to a process for reducing the surface energy of organic materials which comprises incorporating into the organic material at least one compound of the formula I [component b)].

The preferred compounds of the formula I or component (b) respectively, and optionally further additives, in the process for reducing the surface energy [e.g. increasing the oil and water repellency] of organic materials are the same as those described for the composition.

A preferred embodiment of the present invention is also the use of a compound of the formula I [component (b)] as reducer of surface energy [e.g. as oil and water repellency agent] for an organic material.

The preferred compounds of the formula I or component (b) respectively, and optionally further additives, in the use as reducer of surface energy [e.g. increasing the oil and water repellency] of organic materials are the same as those described for the composition.

The present invention further provides novel compounds of the formula I

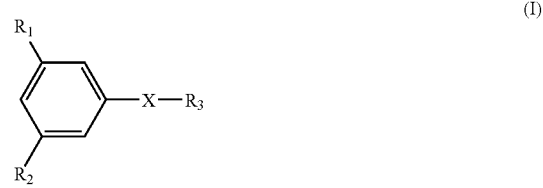

(I)

wherein $R_1$ is —$NO_2$, —N=CH—$R_4$ or

$R_2$ is —X—$R_3$, $R_3$ is a fluorine containing group, $R_4$ is $C_1$-$C_{25}$alkyl, $C_3$-$C_{25}$alkenyl, unsubstituted or $C_1$-$C_4$alkyl substituted phenyl;

$R_5$ is hydrogen, —Y—$R_7$,

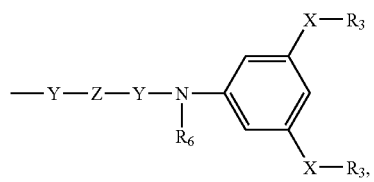

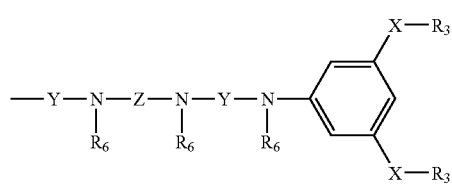

or

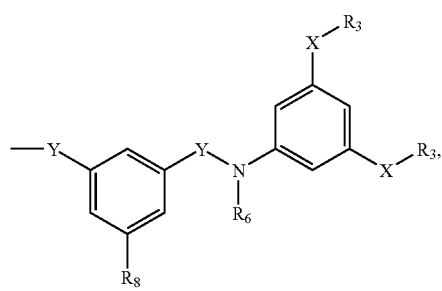

$R_6$ is hydrogen, $C_1$-$C_8$alkyl or benzyl, $R_7$ is $C_1$-$C_{25}$alkyl, $C_2$-$C_{25}$alkenyl, unsubstituted or with $C_1$-$C_4$alkyl or $C_1$-$C_4$alkanoylamino substituted phenyl; unsubstituted or $C_1$-$C_4$alkyl substituted phenylamino;

$R_8$ is —$NO_2$, —N=CH—$R_4$ or

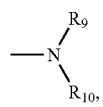

$R_9$ is hydrogen or —Y—$R_7$,

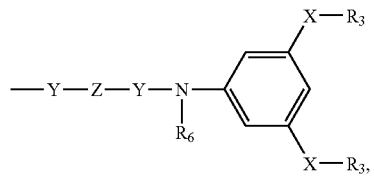

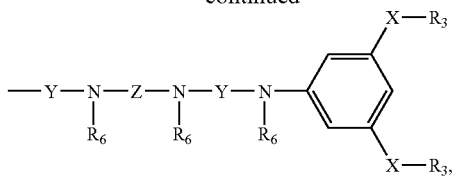

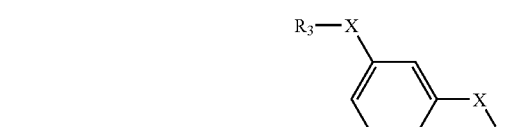

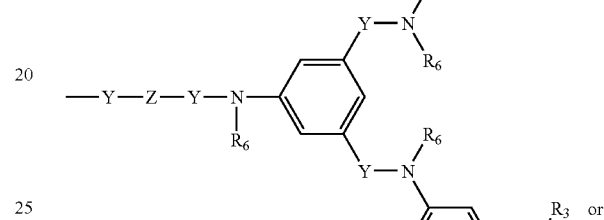

or

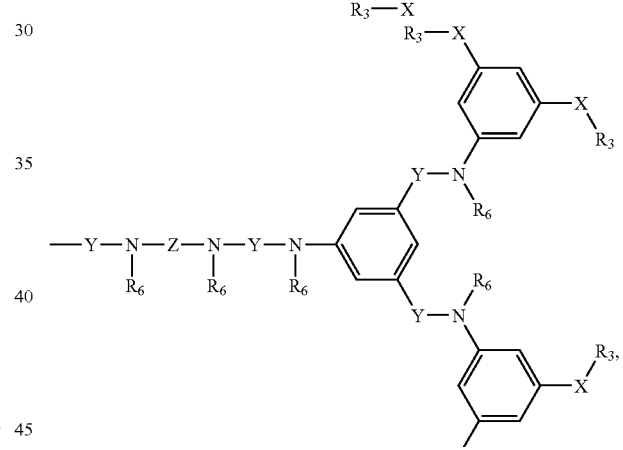

$R_{10}$ is hydrogen, $C_1$-$C_8$alkyl or benzyl,

X is

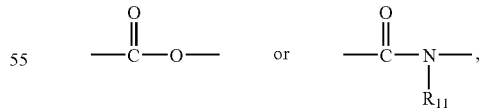

$R_{11}$ is hydrogen, $C_1$-$C_8$alkyl or benzyl,

Y is

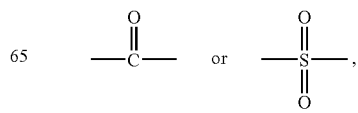

Z is $C_1$-$C_{25}$alkylene, 1,2-phenylene, 1,3-phenylene, 1,4-phenylene or

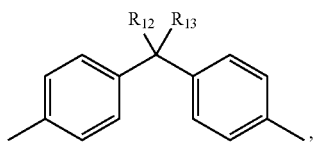

and $R_{12}$ and $R_{13}$ are each independently of one another hydrogen, $C_1$-$C_{12}$alkyl or phenyl, or $R_{11}$, and $R_{12}$ together with the linking carbon atom, form a $C_5$-$C_8$cycloalkylidene ring which is unsubstituted or substituted by 1 to 3 $C_1$-$C_4$alkyl groups.

Of special interest are the compounds of the formula I wherein $R_1$ is —$NO_2$, —N=CH—$R_4$ or

$R_2$ is —X—$R_3$, $R_3$ is —$CH_2CH_2(CF_2)_7CF_3$ or —$CH_2CH_2(CF_2)_3CF_3$, $R_4$ is $C_4$-$C_{12}$alkyl, $C_4$-$C_{12}$alkenyl, unsubstituted or $C_1$-$C_4$alkyl substituted phenyl;

$R_5$ is hydrogen, —Y—$R_7$,

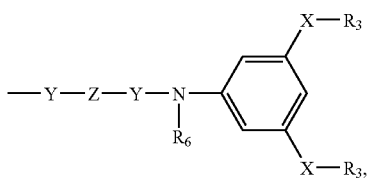

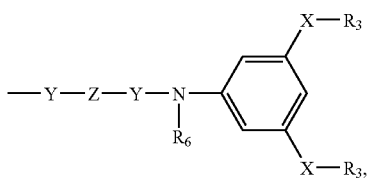

or

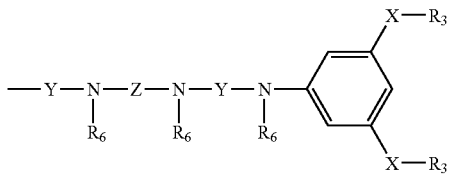

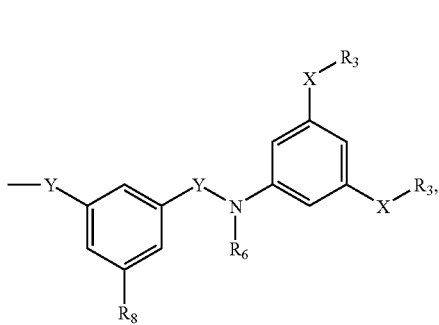

$R_6$ is hydrogen, $R_7$ is $C_1$-$C_8$alkyl, $C_2$-$C_8$alkenyl, phenyl or phenylamino, $R_8$ is —$NO_2$, —N=CH—$R_4$ or

$R_9$ is hydrogen, —Y—$R_7$,

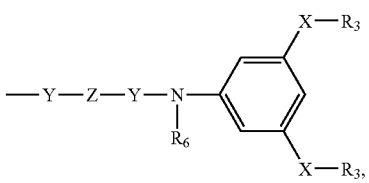

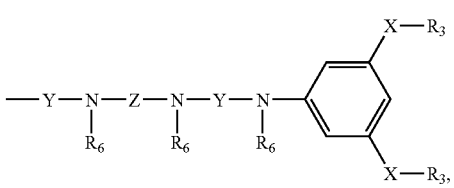

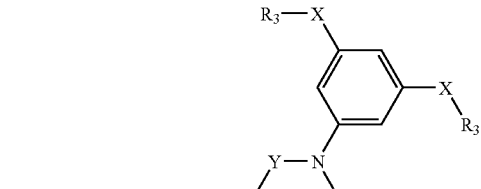

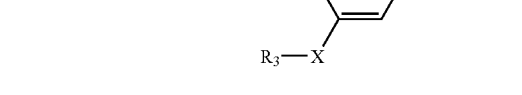

or

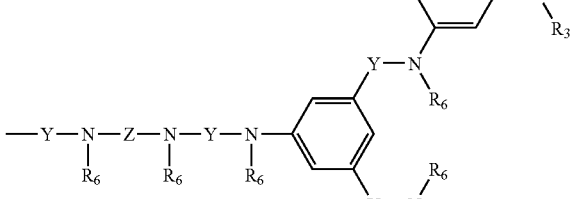

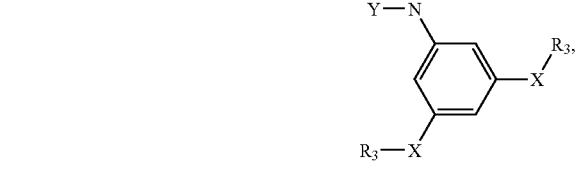

$R_{10}$ is hydrogen,

X is

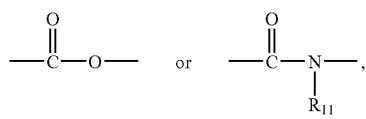

$R_{11}$ is hydrogen,

Y is

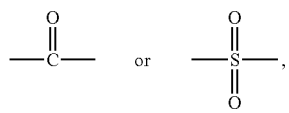

Z is $C_4$-$C_{12}$alkylene, 1,3-phenylene, 1,4-phenylene or

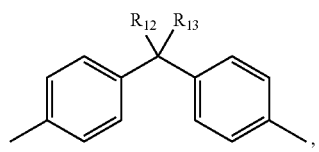

and $R_{12}$ and $R_{13}$ are hydrogen.

The preferred meanings of the general symbols in the novel compounds of the formula Ia are the same as the preferred meanings of the general symbols set out in relation to the compositions of the invention.

The following examples illustrate the invention further. Parts or percentages relate to weight.

EXAMPLE 1

Preparation of the Compound of the Formula 101

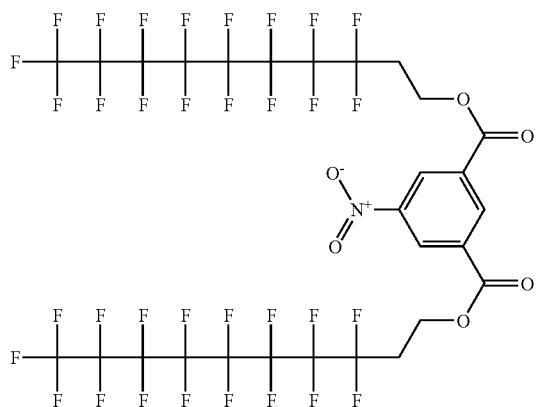

17.8 g (40.0 mmol) of the fluorinated alcohol (Zonyl BA-L) and 4.45 g (44.0 mmol) of triethylamine are dissolved in 50 ml of tetrahydrofuran. 4.96 g (20.0 mmol) of 5-nitroisophthaloyl chloride is dissolved in 10 ml of tetrahydrofuran and slowly dropped to the reaction mixture at 0-10° C. under nitrogen atmosphere. A large mass of a white solid is formed and as the reaction becomes difficult to stir, 90 ml of tetrahydrofuran is added. The reaction mixture is stirred at room temperature for 12 hours. Diethyl ether (200 ml) is added and the organic phase is washed repeatedly with 1N $NH_4Cl$ and water until pH neutral. The organic phase is dried over magnesium sulfate, filtered and concentrated using a vacuum rotary evaporator to give 16.5 g of a yellow solid. The crude solid is purified by recrystallization in tetrahydrofuran/diethyl ether to give 13.1 g of the compound 101, white solid, m.p. 108-110° C. $^1$H NMR: (300 MHz, $CDCl_3$): $\delta$=9.07 (s, ArH, 2H); 9.00 (s, ArH, 1H); 4.76 (t, J=6.3 Hz, $OCH_2CH_2CF_2$, 4H); 2.80-2.55 (m, $OCH_2CH_2CF_2$, 4H).

EXAMPLE 2

Preparation of the Compound of the Formula 102

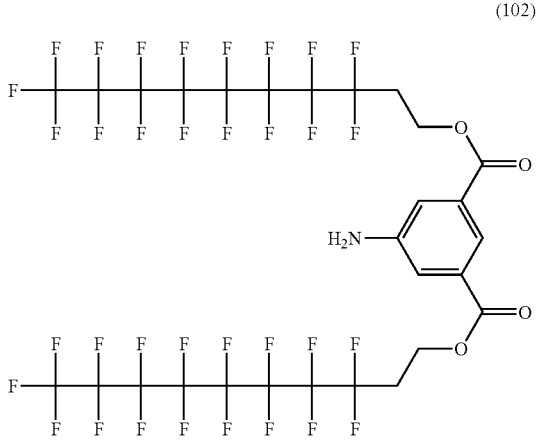

In an autoclave vessel (100 ml Glass-Camile), 8.50 g (8.00 mmol) of the compound of the formula 101 [prepared according to Example 1] and 0.50 g of the catalyst (Pd/C, 10% wt) are dissolved in 50 ml of tetrahydrofuran under inert gas. $H_2$ gas is then loaded until a pressure of 5 bar is obtained in the vessel. The reaction mixture is stirred for 12 hours at 75° C. The reaction mixture is cooled down to room temperature, then the catalyst is filtered off and the solvent is evaporated using a vacuum rotary evaporator to give 6.85 g of the compound 102, pale yellow solid, m.p. 132-133° C. $^1$H NMR: (300 MHz, acetone-$d_6$): $\delta$=7.95-7.90 (m, ArH, 1H); 7.60-7.55

(m, ArH, 2H); 5.31 (br s, NH$_2$, 2H); 4.68 (t, J=6.0 Hz, OCH$_2$CH$_2$CF$_2$, 4H); 3.00-2.55 (m, OCH$_2$CH$_2$CF$_2$, 4H).

EXAMPLE 3

Preparation of the Compound of the Formula 103

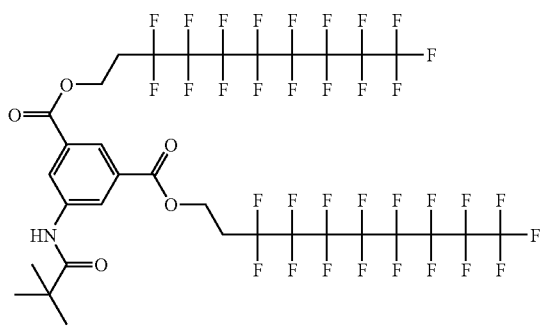

(103)

1.21 g (1.20 mmol) of the compound of the formula 102 [prepared according to Example 2] and 0.14 g (1.40 mmol) of triethylamine are dissolved in 30 ml of tetrahydrofuran. 0.14 g (1.20 mmol) of pivaloyl chloride is added to the reaction mixture at room temperature under nitrogen atmosphere. The reaction mixture is stirred at room temperature for 6 hours. Diethyl ether (80 ml) is added and the organic phase is washed repeatedly with water until pH neutral. The organic phase is dried over magnesium sulfate, filtered and concentrated using a vacuum rotary evaporator to give 1.20 g of a pale brown wax. The crude product is purified by flash chromatography (hexane/ethyl acetate: 2:1) to give 1.10 g of the compound of formula 103, pale yellow wax. $^1$H NMR: (300 MHz, acetone-d$_6$): δ=9.09 (br s, NH, 1H); 8.70-8.65 (m, ArH, 2H); 8.40-8.30 (m, ArH, 1H); 4.74 (t, J=6.0 Hz, OCH$_2$CH$_2$CF$_2$, 4H); 3.00-2.75 (m, OCH$_2$CH$_2$CF$_2$, 4H); 1.34 (s, tert-butyl, 9H).

EXAMPLE 4

Preparation of the Compound of the Formula 104

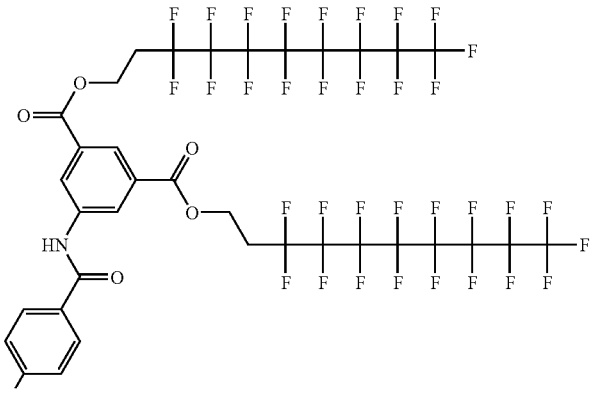

(104)

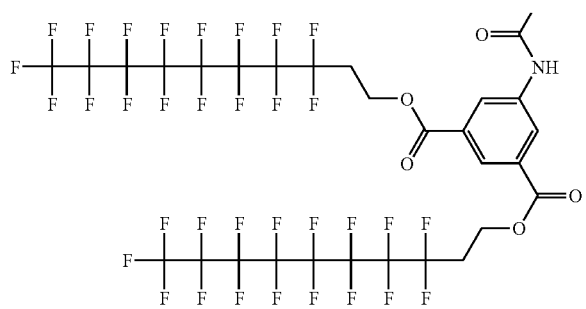

1.51 g (1.50 mmol) of the compound of the formula 102 [prepared according to Example 2] and 0.18 g (1.80 mmol) of triethylamine are dissolved in 40 ml of tetrahydrofuran. 0.15 g (0.70 mmol) of terephthaloyl chloride is added to the reaction mixture at room temperature under nitrogen atmosphere. The reaction mixture is stirred at room temperature for 12 hours. Ethyl acetate (100 ml) and tetrahydrofuran (50 ml) are added and the organic phase is washed repeatedly with water and brine until pH neutral. The aqueous phase is discarded and the material in suspension in the organic phase is filtered off to give 0.95 g of the compound of formula 104, white solid, m.p. 160-268° C. $^1$H NMR: (300 MHz, tetrahydrofuran-$d_8$): δ=9.95 (s, NH, 2H); 8.80-8.70 (m, ArH, 4H); 8.50-8.40 (m, ArH, 2H); 8.20-8.10 (m, ArH, 4H); 4.71 (t, J=6.0 Hz, $OCH_2CH_2CF_2$, 8H); 2.95-2.70 (m, $OCH_2CH_2CF_2$, 8H).

EXAMPLE 5

Preparation of the Compound of the Formula 105

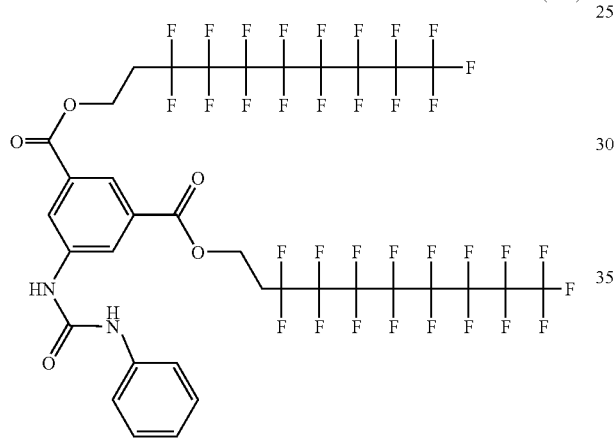

(105)

1.80 g (1.70 mmol) of the compound of the formula 102 [prepared according to Example 2] and 0.21 g (2.10 mmol) of triethylamine are dissolved in 40 ml of tetrahydrofuran. 0.21 g (1.70 mmol) of phenylisocyanate is added to the reaction mixture at room temperature under nitrogen atmosphere. The reaction mixture is stirred at room temperature for 24 hours. Diethyl ether (100 ml) is added and the organic phase is washed repeatedly with 1N $NH_4Cl$, water and brine until pH neutral. The organic phase is dried over magnesium sulfate, filtered and concentrated using a vacuum rotary evaporator to give 2.00 g of a pale yellow solid. The crude product is purified by recrystallization in ethyl acetate to give 0.67 g of the compound of formula 105, white solid, m.p. 164-166° C. $^1$H NMR: (300 MHz, acetone-$d_6$): δ=8.58 (br s, NH, 1H); 8.55-8.45 (m, ArH, 2H); 8.35-8.25 (m, 1H); 8.25-8.15 (m, 1H); 7.65-7.50 (m, ArH, 2H); 7.35-7.20 (m, ArH, 2H); 7.10-6.95 (m, ArH, 1H); 4.74 (t, J=6.0 Hz, $OCH_2CH_2CF_2$, 4H); 3.00-2.70 (m, $OCH_2CH_2CF_2$, 4H).

EXAMPLE 6

Preparation of the Compound of the Formula 106

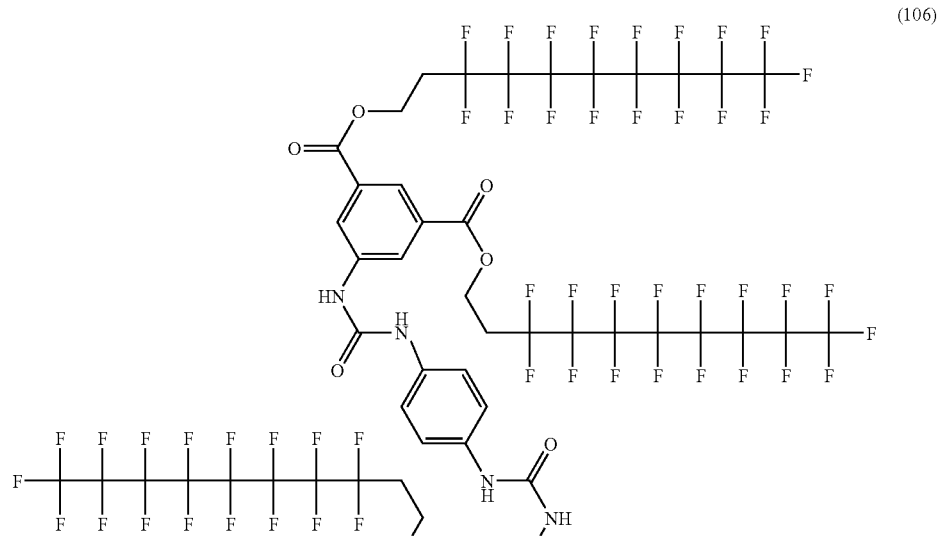

(106)

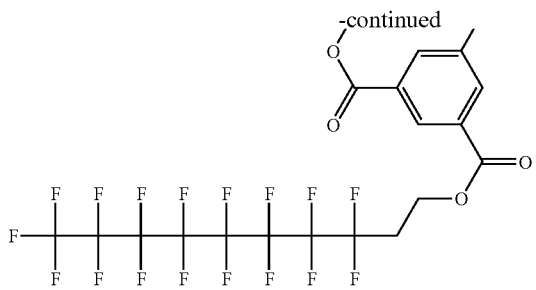

2.25 g (2.18 mmol) of the compound of the formula 102 [prepared according to Example 2] and 0.27 g (2.62 mmol) of triethylamine are dissolved in 50 ml of tetrahydrofuran. 0.17 g (1.09 mmol) of 1,4-phenylenediisocyanate is added to the reaction mixture at room temperature under nitrogen atmosphere. The reaction mixture is stirred at room temperature for 24 hours. Water (50 ml) is added and the reaction mixture is stirred for 15 minutes, then the solid was filtered off and dried in an oven to give the compound of formula 106, white solid, m.p.>200° C.

EXAMPLE 7

Preparation of the Compound of the Formula 107

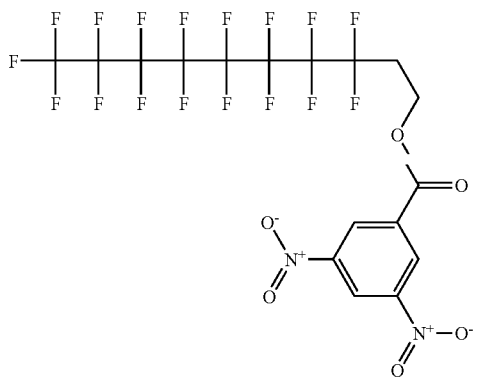

6.92 g (15.6 mmol) of the fluorinated alcohol (Zonyl BA-L) and 2.37 g (23.4 mmol) of triethylamine are dissolved in 40 ml of tetrahydrofuran. 3.60 g (15.6 mmol) of 3,5-dinitrobenzoyl chloride is added portionwise to the reaction mixture at 0-10° C. under nitrogen atmosphere. The reaction mixture is stirred at room temperature for 12 hours. Diethyl ether (100 ml) is added and the organic phase is washed repeatedly with 1N $NH_4Cl$ and water until pH neutral. The organic phase is dried over magnesium sulfate, filtered and concentrated using a vacuum rotary evaporator to give 9.40 g of a yellow solid. The crude product is purified by flash chromatography (hexane/ethyl acetate: 4:1) to give 7.50 g of the compound of formula 107, white solid, m.p. 111-113° C. $^1$H NMR: (300 MHz, $CDCl_3$): δ=9.30-9.25 (m, ArH, 1H); 9.20-9.15 (m, ArH, 2H); 4.80 (t, J=6.3 Hz, $OCH_2CH_2CF_2$, 2H); 2.85-2.60 (m, $OCH_2CH_2CF_2$, 2H).

EXAMPLE 8

Preparation of the Compound of the Formula 108

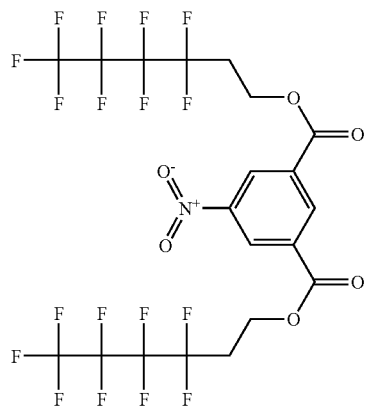

18.8 g (71.1 mmol) of the fluorinated alcohol (Fluorochem Limited) and 8.63 g (85.3 mmol) of triethylamine are dissolved in 120 ml of dry toluene. 8.82 g (35.6 mmol) of 5-nitroisophthaloyl chloride is slowly added portionwise to the reaction mixture at 0-10° C. under nitrogen atmosphere. A large mass of a white solid is formed and as the reaction became difficult to stir, 280 ml of dry toluene is added. The reaction mixture is stirred at room temperature for 12 hours. Then water (300 ml) is added, the suspension is stirred for 1 hour and the solid is filtered off, washed repeatedly with water and dried in an oven to give 14.9 g of the compound of formula 108, white solid, m.p. 91-92° C. $^1$H NMR: (300 MHz, acetone-$d_6$): δ=9.00 (br s, ArH, 2H); 8.95 (br s, ArH, 1H); 4.83 (t, J=6.0 Hz, $OCH_2CH_2CF_2$, 4H); 3.05-2.80 (m, $OCH_2CH_2CF_2$, 4H).

EXAMPLE 9

Preparation of the Compound of the Formula 109

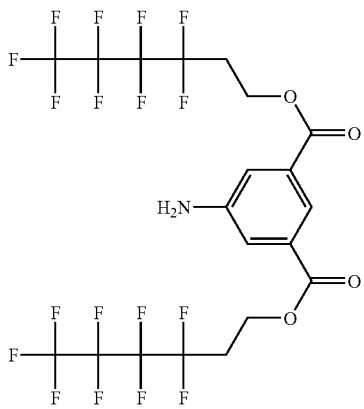

(109)

In an autoclave vessel (100 ml Glass-Camile), 9.80 g (13.9 mmol) of the compound of the formula 108 [prepared according to Example 8] and 0.80 g of the catalyst (Pd/C, 10% wt) are dissolved in 50 ml of tetrahydrofuran under inert gas. $H_2$ gas is then loaded until a pressure of 5 bar is obtained in the vessel. The reaction mixture is stirred for 20 hours at 75° C. The reaction mixture is cooled down to room temperature, then the catalyst is filtered off and the solvent is evaporated using a vacuum rotary evaporator to give 8.00 g of the compound of formula 109, white solid, m.p. 131-133° C. $^1$H NMR: (300 MHz, tetrahydrofuran-$d_8$): δ=8.05 (br s, ArH, 1H); 7.53 (br s, ArH, 2H); 4.65 (t, J=6.3 Hz, OCH$_2$CH$_2$CF$_2$, 4H); 4.00 (br s, NH$_2$, 2H); 2.75-2.50 (m, OCH$_2$CH$_2$CF$_2$, 4H).

EXAMPLE 10

Preparation of the Compound of the Formula 110

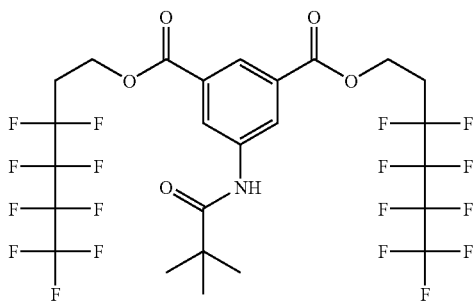

(110)

1.78 g (2.64 mmol) of the compound of the formula 109 [prepared according to Example 9] and 0.38 g (3.70 mmol) of triethylamine are dissolved in 25 ml of tetrahydrofuran. 0.32 g (2.64 mmol) of pivaloyl chloride is added to the reaction mixture at room temperature under nitrogen atmosphere. The reaction mixture is stirred at room temperature for 1 hour. Diethyl ether (80 ml) is added and the organic phase is washed repeatedly with water until pH neutral. The organic phase is dried over magnesium sulfate, filtered and concentrated using a vacuum rotary evaporator to give 1.85 g of the compound of formula 110, pale yellow solid, m.p. 71-73° C. $^1$H NMR: (300 MHz, CDCl$_3$): δ=8.50-8.40 (m, ArH, 2H); 8.45-8.35 (m, ArH, 1H); 7.56 (br s, NH, 1H); 4.67 (t, J=6.3 Hz, OCH$_2$CH$_2$CF$_2$, 4H); 2.75-2.55 (m, OCH$_2$CH$_2$CF$_2$, 4H); 1.36 (s, tBu, 9H).

EXAMPLE 11

Preparation of the Compound of the Formula 111

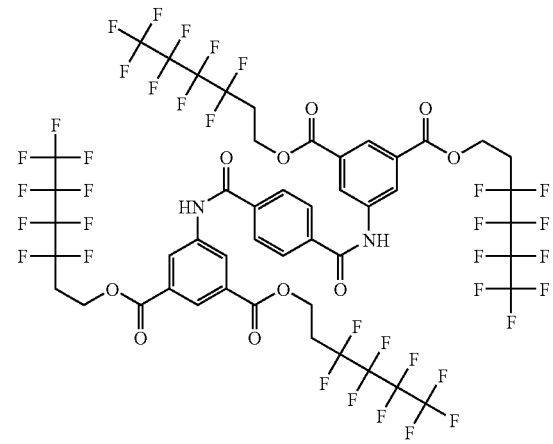

(111)

1.82 g (2.70 mmol) of the compound of the formula 109 [prepared according to Example 9] and 0.33 g (3.24 mmol) of triethylamine are dissolved in 70 ml of tetrahydrofuran. 0.27 g (1.35 mmol) of terephthaloyl chloride is added to the reaction mixture at room temperature under nitrogen atmosphere. The reaction mixture is stirred at room temperature for 2 hours. Ethyl acetate (200 ml) is added and the organic phase is washed repeatedly with water and brine until pH neutral. The organic phase is dried over magnesium sulfate, filtered and concentrated using a vacuum rotary evaporator to give 1.90 g of a pale yellow solid. The crude product is purified by flash chromatography (hexane/ethyl acetate: 2:1) to give 1.70 g of the compound of formula III, white solid, m.p. 187-223° C. $^1$H NMR: (300 MHz, acetone-$d_6$): δ=10.12 (s, NH, 2H); 8.85-8.80 (m, ArH, 4H); 8.45-8.40 (m, ArH, 2H); 8.23 (s, ArH, 4H); 4.77 (t, J=6.0 Hz, OCH$_2$CH$_2$CF$_2$, 8H); 3.00-2.80 (m, OCH$_2$CH$_2$CF$_2$, 8H).

EXAMPLE 12

Preparation of the Compound of the Formula 112

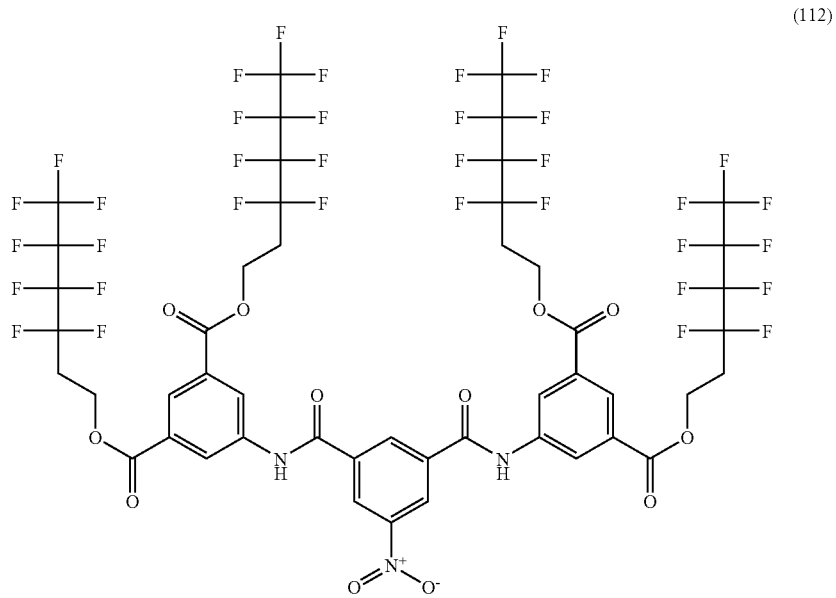

(112)

3.40 g (5.05 mmol) of the compound of the formula 109 [prepared according to Example 9] and 0.62 g (6.07 mmol) of triethylamine are dissolved in 130 ml of tetrahydrofuran. 0.67 g (2.53 mmol) of 5-nitroisophthaloyl chloride is added portionwise to the reaction mixture at room temperature under nitrogen atmosphere. The reaction mixture is stirred at room temperature for 10 hours. Ethyl acetate (300 ml) is added and the organic phase is washed repeatedly with water and brine until pH neutral. The organic phase is dried over magnesium sulfate, filtered and concentrated using a vacuum rotary evaporator to give 3.80 g of a yellow solid. The crude product is purified by flash chromatography (hexane/ethyl acetate: 3:1) to give 0.90 g of the compound of formula 112, yellow solid, m.p. 175-184° C. $^1$H NMR: (300 MHz, acetone-$d_6$): δ=10.50 (s, NH, 2H); 9.10 (s, ArH, 3H); 8.85-8.80 (m, ArH, 4H); 8.50-8.40 (m, ArH, 2H); 4.78 (t, J=6.0 Hz, OCH$_2$CH$_2$CF$_2$, 8H); 3.00-2.80 (m, OCH$_2$CH$_2$CF$_2$, 8H).

EXAMPLE 13

Preparation of the Compound of the Formula 113

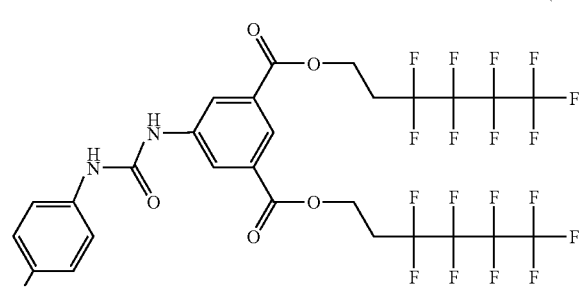

(113)

-continued

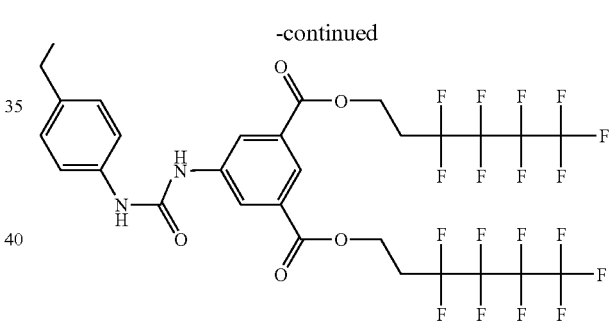

1.50 g (2.23 mmol) of the compound of the formula 109 [prepared according to Example 9] and 0.25 g (2.46 mmol) of triethylamine are dissolved in 50 ml of tetrahydrofuran. 0.28 g (1.12 mmol) of 4,4'-methylene-bis-phenylisocyanate is added to the reaction mixture at room temperature under nitrogen atmosphere. The reaction mixture is stirred at room temperature for 24 hours. Tetrahydrofuran (50 ml) is added and the reaction mixture is stirred for 15 minutes, then the solid was filtered off. The clear colorless mixture is diluted with ethyl acetate, washed with water, dried over magnesium sulfate, filtered and concentrated. The crude material was recrystallized in acetonitrile to give the compound of formula 113, white solid, m.p. 189-191° C. $^1$H NMR: (300 MHz, acetone-$d_6$): δ=8.56 (br s, NH, 2H); 8.52-8.42 (m, ArH, 4H); 8.30-8.20 (m, 2H); 8.19 (br s, NH, 2H); 7.55-7.40 (m, ArH, 4H); 7.22-7.10 (m, ArH, 4H); 4.73 (t, J=6.0 Hz, OCH$_2$CH$_2$CF$_2$, 8H); 3.92 (s, ArCH$_2$Ar, 2H); 3.00-2.70 (m, OCH$_2$CH$_2$CF$_2$, 8H).

EXAMPLE 14

Preparation of the Compound of the Formula 114

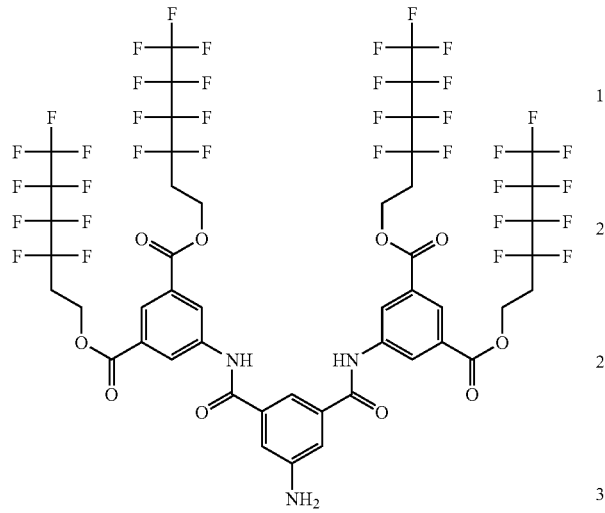

(114)

In an autoclave vessel (100 ml Glass-Camile), 2.30 g (1.51 mmol) of the compound of the formula 112 [prepared according to Example 12] and 0.25 g of the catalyst (Pd/C, 10% wt) are dissolved in 40 ml of tetrahydrofuran under inert gas. H$_2$ gas is then loaded until a pressure of 5 bar is obtained in the vessel. The reaction mixture is stirred for 6 hours at 75° C. The reaction mixture is cooled down to room temperature, then the catalyst is filtered off and the solvent is evaporated using a vacuum rotary evaporator to give 2.10 g of the compound of formula 114, pale yellow solid. $^1$H NMR: (300 MHz, acetone-d$_6$): δ=10.00 (s, NH, 2H); 8.85-8.70 (m, ArH, 4H); 8.45-8.35 (m, ArH, 2H); 7.82 (br s, ArH, 1H); 7.55-7.45 (m, ArH, 2H); 5.26 (br s, NH$_2$, 2H); 4.76 (t, J=6.0 Hz, OCH$_2$CH$_2$CF$_2$, 8H); 3.00-2.75 (m, OCH$_2$CH$_2$CF$_2$, 8H).

EXAMPLE 15

Preparation of the Compound of the Formula 115

(115)

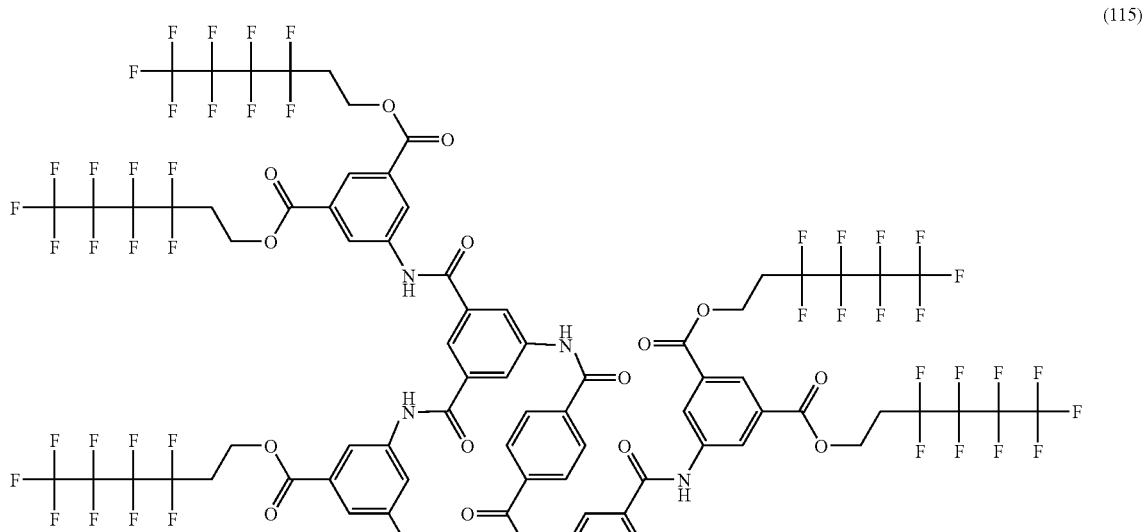

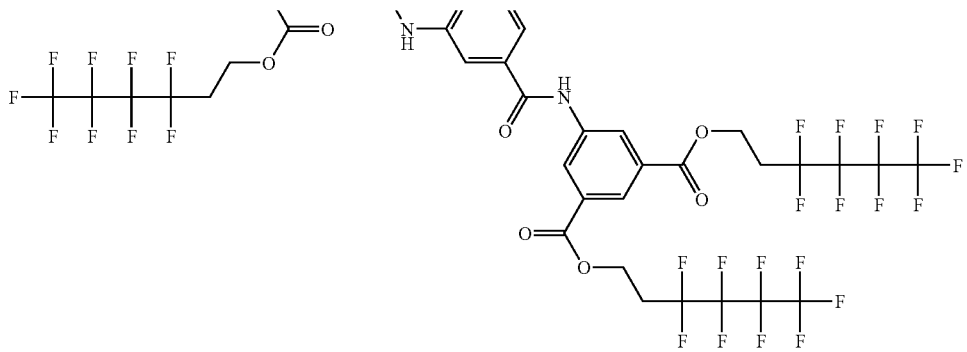

1.95 g (1.31 mmol) of the compound of the formula 114 [prepared according to Example 14] and 0.16 g (1.56 mmol) of triethylamine are dissolved in 30 ml of tetrahydrofuran. 0.13 g (0.65 mmol) of terephthaloyl chloride is added to the reaction mixture at room temperature under nitrogen atmosphere. The reaction mixture is stirred at room temperature for 5 hours. Water (30 ml) is added and the reaction mixture is stirred for 15 minutes, then the solid is filtered off and dried in an oven to give the compound of formula 115, white solid, m.p. 337-347° C. $^1$H NMR: $^1$H NMR: (300 MHz, tetrahydrofuran-d$_8$): δ=10.19 (s, NH, 4H); 10.06 (s, NH, 2H); 8.82-8.75 (m, ArH, 8H); 8.72-8.65 (m, ArH, 4H); 8.50-8.45 (m, ArH, 4H); 8.45-8.35 (m, ArH, 2H); 8.22-8.18 (m, ArH, 4H); 4.72 (t, J=6.0 Hz, OCH$_2$CH$_2$CF$_2$, 16H); 2.95-2.70 (m, OCH$_2$CH$_2$CF$_2$, 16H).

EXAMPLE 16

Water and Oil Repellency in Polypropylene

In order to determine the repellency properties of the compounds of the formula I, they are tested according to the following procedure. The sample preparation is a combination of polypropylene nonwovens and the additive and a thermal treatment (e.g. 130° C. for 10 minutes), which enables the migration of the additive to the surface and a proper surface rearrangement of the chemical groups. This extra heat cycle is needed to melt the compounds of the formula I in order to obtain a homogeneous redistribution over the surface of the substrate. An industrial sample of polypropylene nonwoven, fabric weight: 40 g/m², is dipped into a 1% isopropanol solution of the test compound, simultaneously applying ultrasonic energy for one minute. After that, the sample is dried overnight at room temperature and then two hours at 90° C. in an oven. A part of the sample is afterwards annealed for 10 minutes at 130° C.

The treated nonwoven samples are evaluated in the water repellency test similar to INDA test method 80.8 (99). The wetting behavior of the nonwovens is tested with a series of water/isopropanol mixtures. The observation of the wetting behavior is rated from 0 (water wetting, no repellency) to 10 (optimum water repellency). The results are summarized in Table 1.

TABLE 1

| Example | Compound | Water repellency after drying | Water repellency after annealing |
|---|---|---|---|
| 16a[a] | — | 2 | 2 |
| 16b[b] | 101 | 9 | 10 |

TABLE 1-continued

| Example | Compound | Water repellency after drying | Water repellency after annealing |
|---|---|---|---|
| 16c[b] | 102 | 8 | 9 |
| 16d[b] | 103 | 9 | 9 |
| 16e[b] | 104 | 6 | 9 |
| 16f[b] | 105 | 10 | 10 |
| 16g[b] | 106 | 7 | 9 |
| 16h[b] | 107 | 7 | 8 |
| 16i[b] | 111 | 7 | 7 |
| 16j[b] | 113 | 5 | 5 |
| 16k[b] | 114 | 6 | 6 |
| 16l[b] | 115 | 5 | 6 |

[a] Comparative Example.
[b] Example according to the invention.

The treated nonwoven samples are evaluated in the oil repellency test similar to AATCC test method 118-1997/ISO 14419. This test follows the same concepts of the already described for water repellency test method, but using, as test solvents, a series of hydrocarbons. The observation of the wetting behavior is rated from 0 (no repellency) to 8 (optimum repellency). The results are summarized in Table 2.

TABLE 2

| Example | Compound | Oil repellency after drying | Oil repellency after annealing |
|---|---|---|---|
| 16m[a] | — | 0 | 0 |
| 16n[b] | 101 | 6 | 5 |
| 16o[b] | 103 | 8 | 8 |
| 16p[b] | 105 | 8 | 8 |

[a] Comparative Example.
[b] Example according to the invention.

EXAMPLE 17

Polypropylene Nonwoven Fiber

Compounding: The compound of formula 101 [prepared according to Example 1] is heated in an oven at 70° C. until it is completely liquid. This liquid is added at 10-20 ml/min to a twin-screw extrusion of polypropylene pellets via a heated graduated cylinder using a Leistritz MIC 27/GL-32D twin-screw extruder. The extruder zones are 150°-195° C. with the main screw at 500 RPM and the PP feeder at 200-250 RPM. The molten polymer and additive exit via a two orifice round die. The molten material is immediately cooled and solidified in a cold-water trough. The solidified strand is fed into a Conair/Jetro 304 Pelletizer. The polypropylene used for the spunbond processing is PP 3155 from ExxonMobil (melt flow rate 36 g/10 min) and PP 3546 from ExxonMobil (melt flow rate 1200 g/10 min) for the meltblown processing.

Alternatively, the compound of formula 101 is made into masterbatches by those skilled in the technique. The masterbatch at the desired level is then tumble mixed with the appropriate polypropylene for making spunbond and meltblown nonwovens.

Tumble Mixing The concentrate pellets are let down with additional polypropylene pellets and are mixed with a Marion SPS 1224 mixer, resulting in a desired additive concentration by weight.

Spunbond Process Spunbond nonwoven polypropylene fibers are prepared from the tumble-mixed additive pellets prepared as above using a 1-meter wide Reicofil II Spunbond Pilot Line, under the following conditions: Extruder temperature of 200-220° C. Screen changer temperature of 205° C. Spin pump speed of 9 rpm. 4,000 Hole spinneret with a temperature gradient of 223-240° C. Bonder pressure of 260-300 PLI with bonding temperature of 130-140° C. Cooling air speed of 1700 rpm and suction air speed of 1500 rpm, and collection take up speed is adjusted to produce a nonwoven with a specific basis weight.

Meltblown Process Meltblown polypropylene fibers are also prepared from the tumble-mixed additives pellets prepared as above using 24-inch Reifenhäuser Melt Blowing Pilot Line with Bi-component technology, under the following conditions: Extruder temperature of 160-240° C. for both A & B extruders. Screen changer temperature of 240° C. Spin pump speed of 16 rpm for both A & B extruders. Die temperature gradient of 240° C. Throughput 29.7 kg/h. Suction blower speed of 2000 rpm. Spin belt speed is adjusted to produce a nonwoven with a specific basis weight.

Alternatively: Meltblown polypropylene fibers are also prepared from the tumble-mixed additives pellets prepared as above using a custom-built 6-inch Melt Blowing Pilot Line under the following conditions: Extruder temperature of 175-265° C. Die temperature of 265° C. Throughput 0.49 g/h/m (4.44 kg/h). Spin drum speed is adjusted to produce a nonwoven with a specific basis weight.

The produced nonwoven samples are evaluated on their water/alcohol repellency behavior similar to INDA standards (International Nonwoven and Disposables Association). The results are summarized in Table 3.

TABLE 3

| Example | Compound | Water repellency |
|---------|----------|------------------|
| 17a[a)] | — | 2 |
| 17b[b)] | 1% of compound 101[c)] | 7 |
| 17c[b)] | 2% of compound 101[c)] | 9 |

[a)]Comparative Example.
[b)]Example according to the invention.

What is claimed is:

1. A composition comprising a) an organic material which is susceptible to oxidative, thermal or light-induced degradation, and b) at least a compound of the formula I

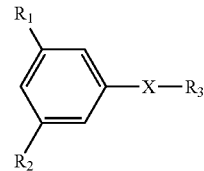

wherein
$R_1$ is —$NO_2$, —N=CH—$R_4$ or

$R_2$ is —X—$R_3$,
$R_3$ is a fluorine containing group,
$R_4$ is $C_1$-$C_{25}$alkyl, $C_3$-$C_{25}$alkenyl, unsubstituted or $C_1$-$C_4$alkyl substituted phenyl;
$R_5$ is hydrogen, —Y—$R_7$,

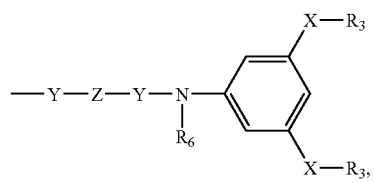

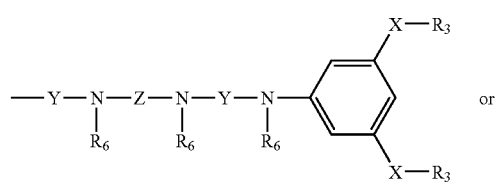

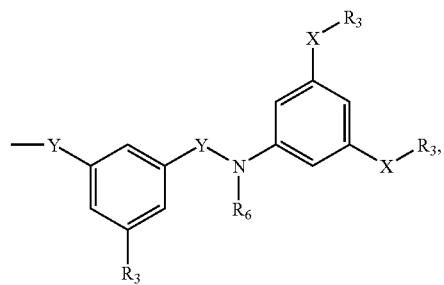

$R_6$ is hydrogen, $C_1$-$C_8$alkyl or benzyl,
$R_7$ is $C_1$-$C_{25}$alkyl, $C_2$-$C_{25}$alkenyl, unsubstituted or $C_1$-$C_4$alkyl or $C_1$-$C_4$alkanoylamino substituted phenyl; unsubstituted or $C_1$-$C_4$alkyl substituted phenylamino;
$R_8$ is —$NO_2$, —N=CH—$R_4$ or

$R_9$ is hydrogen or —Y—$R_7$,

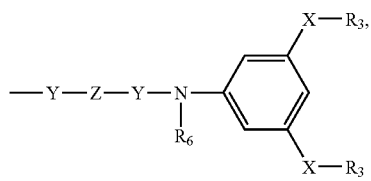

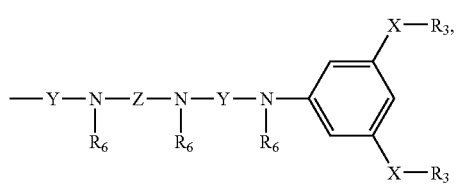

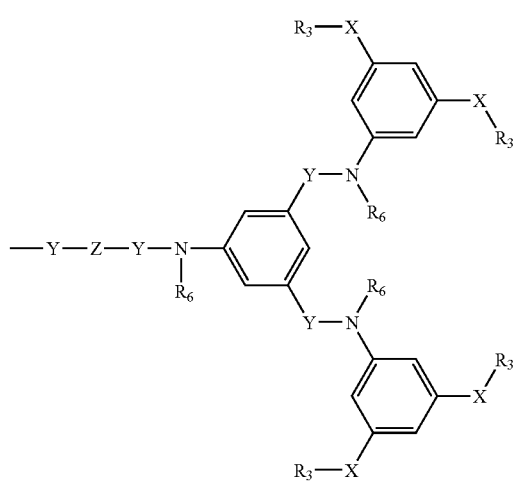

or

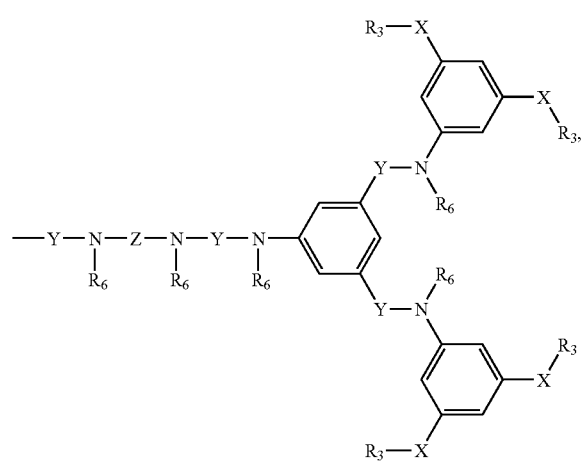

$R_{10}$ is hydrogen, $C_1$-$C_8$alkyl or benzyl,
X is

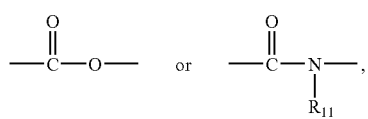

$R_{11}$ is hydrogen, $C_1$-$C_8$alkyl or benzyl,
Y is

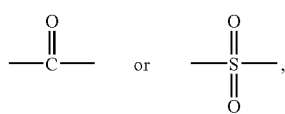

Z is $C_1$-$C_{25}$alkylene, 1,2-phenylene, 1,3-phenylene, 1,4-phenylene

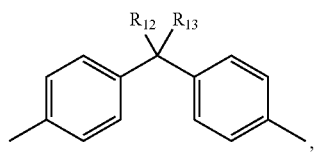

and $R_{12}$ and $R_{13}$ are each independently of one another hydrogen, $C_1$-$C_{12}$alkyl or phenyl, or $R_{11}$ and $R_{12}$ together with the linking carbon atom, form a $C_5$-$C_8$cycloalkylidene ring which is unsubstituted or substituted by 1 to 3 $C_1$-$C_4$alkyl groups.

2. A composition according to claim 1, wherein
$R_3$ is $C_1$-$C_{25}$fluoroalkyl,
X is

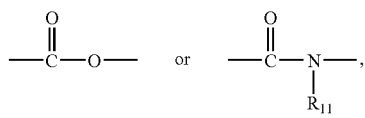

and $R_{11}$ is hydrogen or $C_1$-$C_4$alkyl.

3. A composition according to claim 1, wherein $R_3$ is $C_1$-$C_{25}$fluoroalkyl.

4. A composition according to claim 1, wherein $R_6$ and $R_{10}$ are hydrogen.

5. A composition according to claim 1, wherein $R_7$ is $C_1$-$C_{18}$alkyl, $C_2$-$C_{18}$alkenyl, unsubstituted or $C_1$-$C_4$alkyl or $C_1$-$C_4$alkanoylamino substituted phenyl; unsubstituted or $C_1$-$C_4$alkyl substituted phenylamino.

6. A composition according to claim 1, wherein $R_{12}$ and $R_{13}$ are each independently of one another hydrogen or $C_1$-$C_4$alkyl, or $R_{12}$ and $R_{13}$ together with the linking carbon atom, form a cyclohexylidene ring.

7. A composition according to claim 1, wherein
$R_1$ is —$NO_2$, —N=CH—$R_4$ or

$R_2$ is —X—$R_3$,
$R_3$ is —$CH_2CH_2(CF_2)_7CF_3$ or —$CH_2CH_2(CF_2)_3CF_3$,

R₄ is C₄-C₁₂alkyl, C₄-C₁₂alkenyl, unsubstituted or C₁-C₄alkyl substituted phenyl;
R₅ is hydrogen, —Y—R₇,
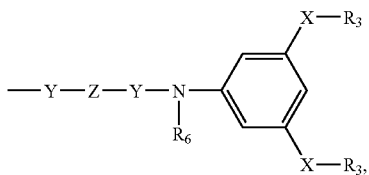
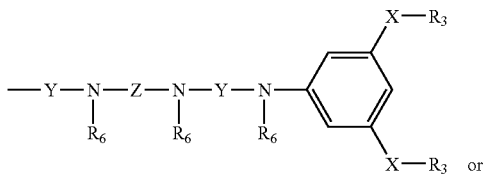 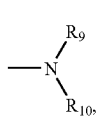 or
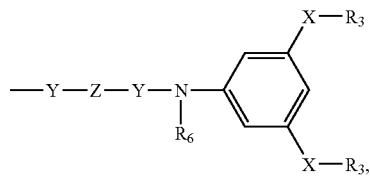
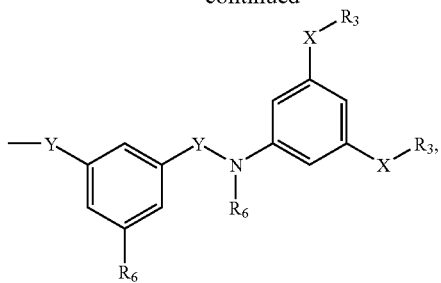
R₆ is hydrogen,
R₇ is C₁-C₈alkyl, C₂-C₈alkenyl, phenyl or phenylamino,
R₈ is —NO₂, —N=CH—R₄ or
$$-N\begin{matrix}R_9\\R_{10},\end{matrix}$$
R₉ is hydrogen, —Y—R₇,
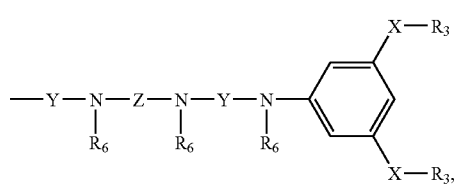
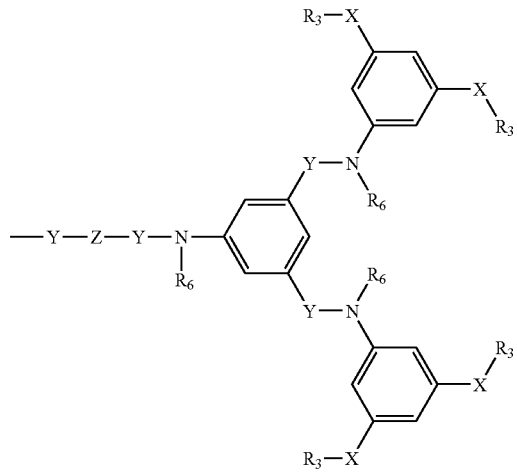 or -continued

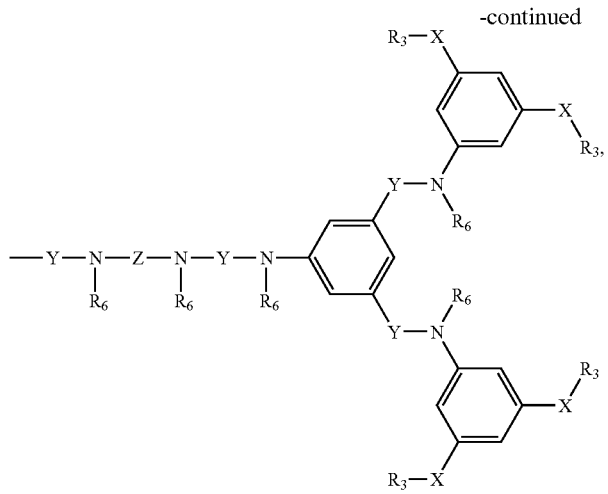

$R_{10}$ is hydrogen,
X is

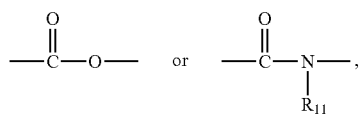

$R_{11}$ is hydrogen,
Y is

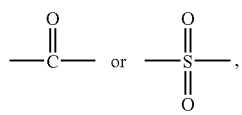

Z is $C_4$-$C_{12}$alkylene, 1,3-phenylene, 1,4-phenylene or

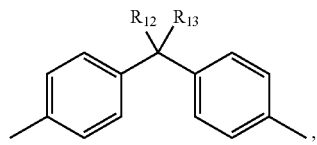

and
$R_{12}$ and $R_{13}$ are hydrogen.

8. A composition according to claim 1 wherein component (a) is a natural or synthetic polymer.

9. A composition according to claim 1 wherein component (a) is a synthetic polymer.

10. A composition according to claim 1 wherein component (a) is a fiber or nonwoven.

11. A composition according to claim 1 wherein component (b) is present in an amount of from 0.01 to 10%, based on the weight of component (a).

12. A composition according to claim 1, comprising in addition, besides components (a) and (b), further additives.

13. A composition according to claim 12, comprising as further additives phenolic antioxidants, light-stabilizers and/or processing stabilizers.

14. A compound of the formula I

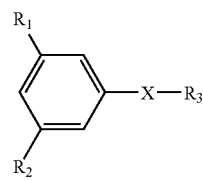

wherein
$R_1$ is —$NO_2$, —N=CH—$R_4$ or

$R_2$ is —X—$R_3$,
$R_3$ is a fluorine containing group,
$R_4$ is $C_1$-$C_{25}$alkyl, $C_3$-$C_{25}$alkenyl, unsubstituted or $C_1$-$C_4$alkyl substituted phenyl;
$R_5$ is hydrogen, —Y—$R_7$,

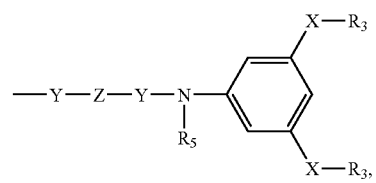

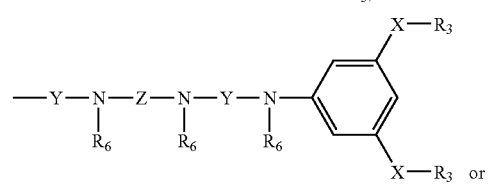

-continued

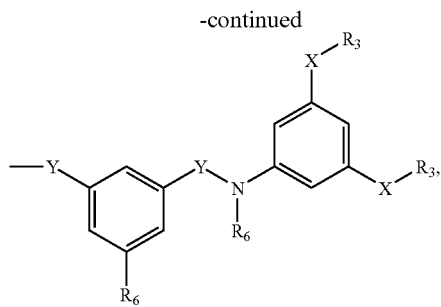

R$_6$ is hydrogen, C$_1$-C$_8$alkyl or benzyl,
R$_7$ is C$_1$-C$_{25}$alkyl, C$_2$-C$_{25}$alkenyl, unsubstituted or C$_1$-C$_4$alkyl or C$_1$-C$_4$alkanoylamino substituted phenyl; unsubstituted or C$_1$-C$_4$alkyl substituted phenylamino;
R$_8$ is —NO$_2$, —N=CH—R$_4$ or

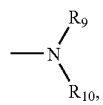

R$_9$ is hydrogen or —Y—R$_7$,

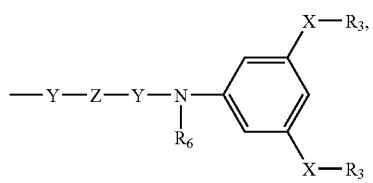

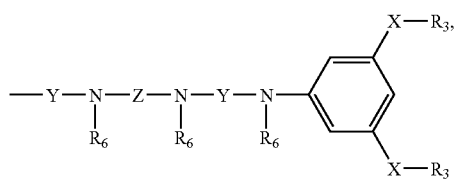

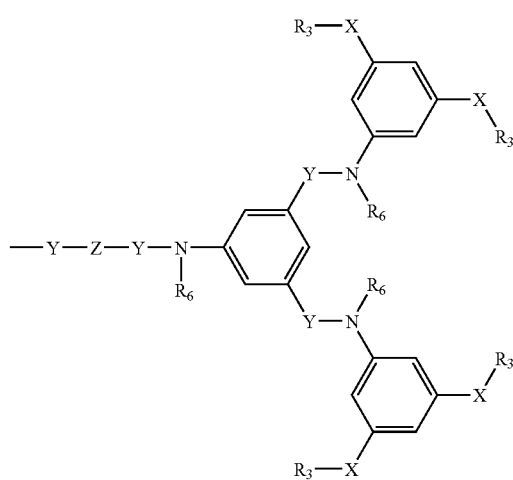

-continued

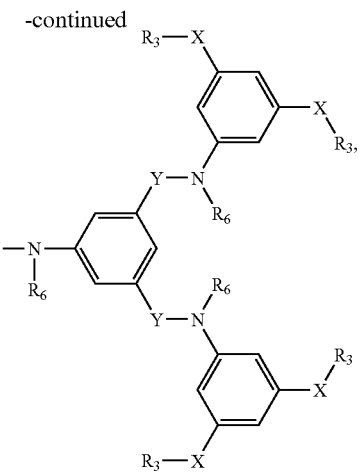

R$_{10}$ is hydrogen, C$_1$-C$_8$alkyl or benzyl,
X is

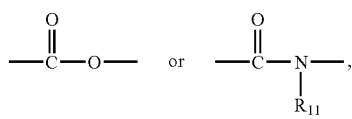

R$_{11}$ is hydrogen, C$_1$-C$_8$alkyl or benzyl,
Y is

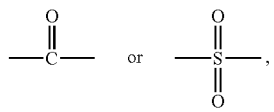

Z is C$_1$-C$_{25}$alkylene, 1,2-phenylene, 1,3-phenylene, 1,4-phenylene or

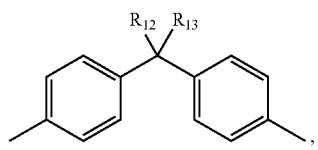

and
R$_{12}$ and R$_{13}$ are each independently of one another hydrogen, C$_1$-C$_{12}$alkyl or phenyl, or R$_{11}$ and R$_{12}$ together with the linking carbon atom, form a C$_5$-C$_8$cycloalkylidene ring which is unsubstituted or substituted by 1 to 3 C$_1$-C$_4$alkyl groups.

15. A compound according to claim 14, wherein
R$_1$ is —NO$_2$, —N=CH—R$_4$ or

$R_2$ is —X—$R_3$,
$R_3$ is —CH$_2$CH$_2$(CF$_2$)$_7$CF$_3$ or —CH$_2$CH$_2$(CF$_2$)$_3$CF$_3$,
$R_4$ is C$_4$-C$_{12}$alkyl, C$_4$-C$_{12}$alkenyl, unsubstituted or C$_1$-C$_4$alkyl substituted phenyl;
$R_5$ is hydrogen, —Y—$R_7$,
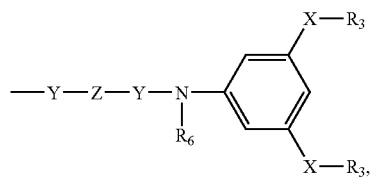
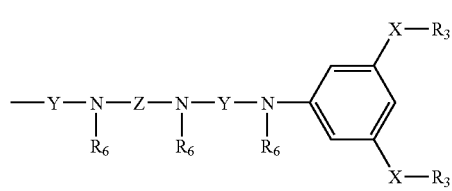
or
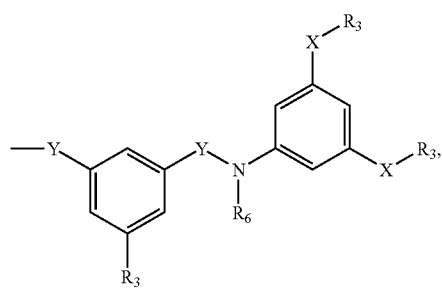
$R_6$ is hydrogen,
$R_7$ is C$_1$-C$_8$alkyl, C$_2$-C$_8$alkenyl, phenyl or phenylamino,
$R_8$ is —NO$_2$, —NCH—$R_4$ or
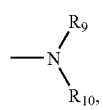
$R_9$ is hydrogen, —Y—$R_7$,
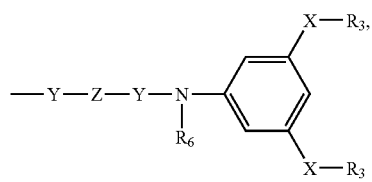
-continued
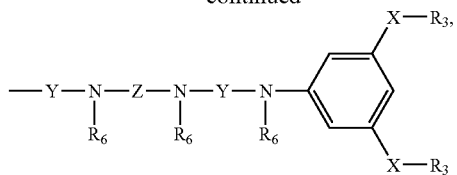
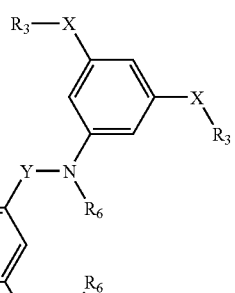
or
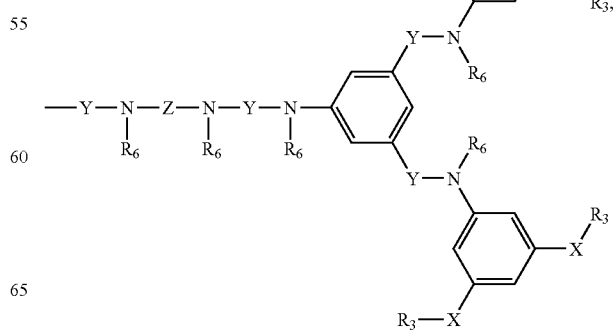

$R_{10}$ is hydrogen,
X is
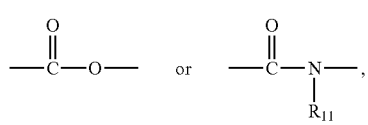
$R_{11}$ is hydrogen,
Y is
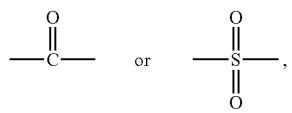
Z is $C_4$-$C_{12}$alkylene, 1,3-phenylene, 1,4-phenylene or
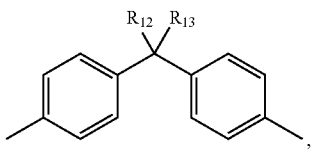
and
$R_{12}$ and $R_{13}$ are hydrogen.
16. A process for reducing the surface energy of organic materials which comprises incorporating into the organic material at least one component (b) according to claim 1.
* * * * *